(12) United States Patent
Nordstrom et al.

(10) Patent No.: US 6,847,490 B1
(45) Date of Patent: Jan. 25, 2005

(54) OPTICAL PROBE ACCESSORY DEVICE FOR USE IN VIVO DIAGNOSTIC PROCEDURES

(75) Inventors: Robert Nordstrom, Hanover, MA (US); David Bee, Groton, MA (US); Mark Modell, Natick, MA (US); Ze'ev Hed, Nashua, NH (US); Jennie Kwo, Cambridge, MA (US); Matthew Emans, Boston, MA (US)

(73) Assignee: MediSpectra, Inc., Lexington, MA (US)

( * ) Notice: Subject to any disclaimer, the term of this patent is extended or adjusted under 35 U.S.C. 154(b) by 593 days.

(21) Appl. No.: 09/591,706

(22) Filed: Jun. 9, 2000

Related U.S. Application Data

(63) Continuation-in-part of application No. 09/481,762, filed on Jan. 11, 2000, and a continuation-in-part of application No. 09/241,806, filed on Feb. 2, 1999, now Pat. No. 6,411,835, which is a continuation-in-part of application No. 08/782,936, filed on Jan. 13, 1997, now Pat. No. 6,104,945.
(60) Provisional application No. 60/138,235, filed on Jun. 9, 1999, and provisional application No. 60/115,373, filed on Jan. 11, 1999.

(51) Int. Cl.$^7$ .......................... G02B 3/00; A61B 5/05; A61B 6/00
(52) U.S. Cl. .................... 359/642; 600/407; 600/473; 600/476
(58) Field of Search .................. 359/642; 600/407, 600/473, 476

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt et al. | 128/2 |
| D242,393 S | 11/1976 | Bauman | |
| D242,396 S | 11/1976 | Bauman | |
| D242,397 S | 11/1976 | Bauman | |
| D242,398 S | 11/1976 | Bauman | |
| 4,017,192 A | 4/1977 | Rosenthal et al. | 356/201 |
| 4,071,020 A | 1/1978 | Pugliese et al. | 128/2 |
| 4,198,571 A | 4/1980 | Sheppard | 250/571 |

(List continued on next page.)

FOREIGN PATENT DOCUMENTS

| | | |
|---|---|---|
| EP | 0 135 134 A2 | 3/1985 |
| EP | 0 280 418 | 8/1988 |
| EP | 0 335 725 | 10/1989 |
| EP | 0 444 689 A2 | 9/1991 |
| EP | 0 474 264 | 3/1992 |

(List continued on next page.)

OTHER PUBLICATIONS

European Search Report for Pending European Patent Application No. 02019837-0, Jan. 14, 2004, 4 pgs.

Ko et al., "Multiresolution Registration of Coronary Artery Image Sequences," *International Journal of Medical Informatics*, vol. 44 (1997), pp. 93–104.

(List continued on next page.)

*Primary Examiner*—Scott J. Sugarman
(74) *Attorney, Agent, or Firm*—Testa, Hurwitz & Thibeault, LLP

(57) ABSTRACT

The present invention recognizes that optical probes function both as medical access devices and as instruments which collect complex optical data. The invention provides an optical probe accessory device which can access luminal spaces within the body of a patient without sacrificing the quality of optical data obtained. The accessory device further comprises either, singly, or in combination, selectable features or options which optimize light transmission, maximize patient comfort, and provide single-use capabilities.

38 Claims, 5 Drawing Sheets

U.S. PATENT DOCUMENTS

| | | | |
|---|---|---|---|
| 4,218,703 A | 8/1980 | Netravali et al. | 358/136 |
| 4,254,421 A | 3/1981 | Kreutel, Jr. | 343/754 |
| 4,273,110 A | 6/1981 | Groux | 128/6 |
| 4,357,075 A | 11/1982 | Hunter | 350/294 |
| 4,397,557 A | 8/1983 | Herwig et al. | 356/342 |
| 4,515,165 A | 5/1985 | Carroll | 128/664 |
| 4,549,229 A | 10/1985 | Nakano et al. | 360/8 |
| 4,558,462 A | 12/1985 | Horiba et al. | 382/42 |
| 4,641,352 A | 2/1987 | Fenster et al. | 382/6 |
| 4,646,722 A | 3/1987 | Silverstein et al. | 128/4 |
| 4,662,360 A | 5/1987 | O'Hara et al. | 128/9 |
| 4,733,063 A | 3/1988 | Kimura et al. | 250/201 |
| 4,741,326 A | 5/1988 | Sidall et al. | 128/4 |
| 4,753,530 A | 6/1988 | Knight et al. | 356/73 |
| 4,768,513 A | 9/1988 | Suzuki | 128/634 |
| 4,800,571 A | 1/1989 | Konishi | 375/10 |
| 4,844,617 A | 7/1989 | Kelderman et al. | 356/372 |
| 4,845,352 A | 7/1989 | Benschop | 250/201 |
| 4,852,955 A | 8/1989 | Doyle et al. | 350/1.2 |
| 4,877,033 A | 10/1989 | Seitz, Jr. | 128/660.05 |
| 4,878,485 A | 11/1989 | Adair | 128/6 |
| 4,891,829 A | 1/1990 | Deckman et al. | 378/4 |
| 4,930,516 A | 6/1990 | Alfano et al. | 128/665 |
| 4,945,478 A | 7/1990 | Merickel et al. | 364/413.22 |
| 4,965,441 A | 10/1990 | Picard | 250/201.3 |
| 4,972,258 A | 11/1990 | Wolf et al. | 358/93 |
| 4,974,580 A | 12/1990 | Anapliotis | 128/4 |
| 4,979,498 A | 12/1990 | Oneda et al. | 128/6 |
| 4,997,242 A | 3/1991 | Amos | 350/6.91 |
| 5,003,979 A | 4/1991 | Merickel et al. | 364/413.22 |
| 5,011,243 A | 4/1991 | Doyle et al. | 350/1.2 |
| 5,022,757 A | 6/1991 | Modell | 356/318 |
| 5,028,802 A | 7/1991 | Webb et al. | 250/571 |
| 5,032,720 A | 7/1991 | White | 250/236 |
| 5,034,613 A | 7/1991 | Denk et al. | 250/458.1 |
| 5,036,853 A | 8/1991 | Jeffcoat et al. | 128/634 |
| 5,042,494 A | 8/1991 | Alfano | 128/665 |
| 5,048,946 A | 9/1991 | Sklar et al. | 351/206 |
| 5,054,926 A | 10/1991 | Dabbs et al. | 356/345 |
| 5,065,008 A | 11/1991 | Hakamata et al. | 250/216 |
| 5,071,246 A | 12/1991 | Blaha et al. | 351/221 |
| 5,074,306 A | 12/1991 | Green et al. | 128/664 |
| 5,083,220 A | 1/1992 | Hill | 359/234 |
| 5,091,652 A | 2/1992 | Mathies et al. | 250/458.1 |
| 5,101,825 A | 4/1992 | Gravenstein et al. | 128/633 |
| 5,120,953 A | 6/1992 | Harris | 250/227.2 |
| 5,122,653 A | 6/1992 | Ohki | 250/216 |
| 5,132,526 A | 7/1992 | Iwasaki | 250/201.3 |
| 5,139,025 A | 8/1992 | Lewis et al. | 128/665 |
| 5,154,166 A | 10/1992 | Chikama | 128/4 |
| 5,159,919 A | 11/1992 | Chikama | 128/4 |
| 5,161,053 A | 11/1992 | Dabbs | 359/384 |
| 5,162,641 A | 11/1992 | Fountain | 250/201.2 |
| 5,162,941 A | 11/1992 | Favro et al. | 359/386 |
| 5,168,157 A | 12/1992 | Kimura | 250/234 |
| 5,192,980 A | 3/1993 | Dixon et al. | 356/326 |
| 5,193,525 A | 3/1993 | Silverstein et al. | 128/4 |
| RE34,214 E | 4/1993 | Carlsson et al. | 358/93 |
| 5,199,431 A | 4/1993 | Kittrell et al. | 128/634 |
| 5,201,318 A | 4/1993 | Rava et al. | 128/665 |
| 5,201,908 A | 4/1993 | Jones | 128/4 |
| 5,203,328 A | 4/1993 | Samuels et al. | 128/633 |
| 5,225,671 A | 7/1993 | Fukuyama | 250/216 |
| 5,235,457 A | 8/1993 | Lichtman et al. | 359/368 |
| 5,237,984 A | 8/1993 | Williams, III et al. | 128/4 |
| 5,239,178 A | 8/1993 | Derndinger et al. | 250/234 |
| 5,248,876 A | 9/1993 | Kerstens et al. | 250/561 |
| 5,253,071 A | 10/1993 | MacKay | 358/222 |
| 5,257,617 A | 11/1993 | Takahashi | 128/4 |
| 5,260,569 A | 11/1993 | Kimura | 250/234 |
| 5,260,578 A | 11/1993 | Bliton et al. | 250/461.1 |
| 5,261,410 A | 11/1993 | Alfano et al. | 128/664 |
| 5,262,646 A | 11/1993 | Booker et al. | 250/341 |
| 5,274,240 A | 12/1993 | Mathies et al. | 250/458.1 |
| 5,284,149 A | 2/1994 | Dhadwal et al. | 128/665 |
| 5,286,964 A | 2/1994 | Fountain | 250/201.2 |
| 5,289,274 A | 2/1994 | Kondo | 348/208 |
| 5,294,799 A | 3/1994 | Aslund et al. | 250/458.1 |
| 5,296,700 A | 3/1994 | Kumagai | 250/216 |
| 5,303,026 A | 4/1994 | Strobl et al. | 356/318 |
| 5,306,902 A | 4/1994 | Goodman | 250/201.3 |
| 5,313,567 A | 5/1994 | Civanlar et al. | 395/124 |
| 5,319,200 A | 6/1994 | Rosenthal et al. | 250/341 |
| 5,321,501 A | 6/1994 | Swanson et al. | 356/345 |
| 5,324,979 A | 6/1994 | Rosenthal | 250/504 R |
| 5,325,846 A | 7/1994 | Szabo | 128/4 |
| 5,329,352 A | 7/1994 | Jacobsen | 356/301 |
| 5,337,734 A | 8/1994 | Saab | 128/4 |
| 5,343,038 A | 8/1994 | Nishiwaki et al. | 250/234 |
| 5,345,306 A | 9/1994 | Ichimura et al. | 356/346 |
| 5,345,941 A | 9/1994 | Rava et al. | 128/665 |
| 5,349,961 A | 9/1994 | Stoddart et al. | 128/665 |
| 5,398,685 A | 3/1995 | Wilk et al. | 128/653.1 |
| 5,402,768 A | 4/1995 | Adair | 128/4 |
| 5,406,939 A | 4/1995 | Bala | 128/4 |
| 5,413,092 A | 5/1995 | Williams, III et al. | 128/4 |
| 5,413,108 A | 5/1995 | Alfano | 128/665 |
| 5,415,157 A | 5/1995 | Welcome | 128/4 |
| 5,418,797 A | 5/1995 | Bashkansky et al. | 372/3 |
| 5,419,311 A | 5/1995 | Yabe et al. | 128/4 |
| 5,419,323 A | 5/1995 | Kittrell et al. | 128/653 |
| 5,421,337 A | 6/1995 | Richards-Kortum et al. | 128/665 |
| 5,421,339 A | 6/1995 | Ramanujam et al. | 128/665 |
| 5,424,543 A | 6/1995 | Dombrowski et al. | 250/330 |
| 5,450,857 A | 9/1995 | Garfield et al. | 128/778 |
| 5,451,931 A | 9/1995 | Muller et al. | 340/630 |
| 5,458,132 A | 10/1995 | Yabe et al. | 128/4 |
| 5,458,133 A | 10/1995 | Yabe et al. | 600/121 |
| 5,467,767 A | 11/1995 | Alfano et al. | 128/665 |
| 5,469,853 A | 11/1995 | Law et al. | 128/662.06 |
| 5,477,382 A | 12/1995 | Pernick | 359/559 |
| 5,480,775 A | 1/1996 | Ito et al. | 435/7.2 |
| 5,493,444 A | 2/1996 | Khoury et al. | 359/559 |
| 5,496,259 A | 3/1996 | Perkins | 600/124 |
| 5,507,295 A | 4/1996 | Skidmore | 600/121 |
| 5,516,010 A | 5/1996 | O'Hara et al. | 600/122 |
| 5,519,545 A | 5/1996 | Kawahara | 360/46 |
| 5,529,235 A | 6/1996 | Boiarski et al. | 227/175.1 |
| 5,536,236 A | 7/1996 | Yabe et al. | 600/125 |
| 5,545,121 A | 8/1996 | Yabe et al. | 600/121 |
| 5,551,945 A | 9/1996 | Yabe et al. | 600/122 |
| 5,556,367 A | 9/1996 | Yabe et al. | 600/124 |
| 5,562,100 A | 10/1996 | Kittrell et al. | 128/665 |
| 5,579,773 A | 12/1996 | Vo-Dinh et al. | 128/665 |
| 5,582,168 A | 12/1996 | Samuels et al. | 128/633 |
| 5,587,832 A | 12/1996 | Krause | 359/385 |
| 5,596,992 A | 1/1997 | Haaland et al. | 128/664 |
| 5,599,717 A | 2/1997 | Vo-Dinh | 436/63 |
| 5,609,560 A | 3/1997 | Ichikawa et al. | 600/101 |
| 5,612,540 A | 3/1997 | Richards-Kortum et al. | 250/461.2 |
| 5,623,932 A | 4/1997 | Ramanujam et al. | 128/665 |
| 5,643,175 A | 7/1997 | Adair | 600/133 |
| 5,647,368 A | 7/1997 | Zeng et al. | 128/665 |
| 5,662,588 A | 9/1997 | Lida | 600/121 |
| 5,685,822 A | 11/1997 | Harhen | 600/125 |
| 5,690,106 A | 11/1997 | Bani-Hashemi et al. | 128/653.1 |
| 5,693,043 A | 12/1997 | Kittrell et al. | 606/15 |
| 5,695,448 A | 12/1997 | Kimura et al. | 600/121 |

| | | |
|---|---|---|
| 5,697,373 A | 12/1997 | Richards-Kortum et al. ............. 128/664 |
| 5,699,795 A | 12/1997 | Richards-Kortum et al. ............. 128/634 |
| 5,704,892 A | 1/1998 | Adair ..................... 600/121 |
| 5,707,343 A | 1/1998 | O'Hara et al. ............. 600/121 |
| 5,713,364 A | 2/1998 | DeBaryshe et al. ......... 128/664 |
| 5,717,209 A | 2/1998 | Bigman et al. .......... 250/339.12 |
| 5,720,293 A * | 2/1998 | Quinn et al. ............... 600/505 |
| 5,730,701 A | 3/1998 | Furukawa et al. .......... 600/127 |
| 5,733,244 A | 3/1998 | Yasui et al. .............. 600/127 |
| 5,735,276 A | 4/1998 | Lemelson et al. ......... 128/653 |
| 5,746,695 A | 5/1998 | Yasui et al. .............. 600/127 |
| 5,768,333 A | 6/1998 | Abdel-Mottaleb ........... 378/37 |
| 5,769,792 A | 6/1998 | Palcic et al. ............. 600/477 |
| 5,773,835 A | 6/1998 | Sinofsky et al. ......... 250/462.1 |
| 5,791,346 A | 8/1998 | Craine et al. ............ 128/653 |
| 5,795,632 A | 8/1998 | Buchalter ................ 428/35.2 |
| 5,800,350 A | 9/1998 | Coppleson et al. ......... 600/372 |
| 5,807,248 A | 9/1998 | Mills ..................... 600/322 |
| 5,813,987 A | 9/1998 | Modell et al. ............. 600/473 |
| 5,817,015 A | 10/1998 | Adair ..................... 600/121 |
| 5,830,146 A | 11/1998 | Skladnev et al. .......... 600/478 |
| 5,833,617 A | 11/1998 | Hayashi ................... 600/476 |
| 5,840,035 A | 11/1998 | Heusmann et al. ........... 600/47 |
| 5,842,995 A | 12/1998 | Mahadevan-Jansen et al. ............. 600/473 |
| 5,855,551 A | 1/1999 | Sklandnev et al. ......... 600/372 |
| 5,860,913 A | 1/1999 | Yamaya et al. ............ 600/127 |
| 5,863,287 A | 1/1999 | Segawa .................... 600/121 |
| 5,865,726 A | 2/1999 | Katsurada et al. .......... 600/127 |
| 5,876,329 A | 3/1999 | Harhen .................... 600/125 |
| 5,920,399 A | 7/1999 | Sandison et al. ........... 356/418 |
| 5,921,926 A | 7/1999 | Rolland et al. ............ 600/407 |
| 5,929,985 A | 7/1999 | Sandison et al. ........... 365/318 |
| 5,931,779 A | 8/1999 | Arakaki et al. ............ 600/310 |
| 5,938,617 A | 8/1999 | Vo-Dinh ................... 600/476 |
| 5,941,834 A | 8/1999 | Skladnev et al. .......... 600/587 |
| 5,983,125 A | 11/1999 | Alfano et al. ............ 600/473 |
| 5,987,343 A * | 11/1999 | Kinast .................... 600/323 |
| 5,989,184 A | 11/1999 | Blair et al. .............. 600/167 |
| 5,991,653 A | 11/1999 | Richards-Kortum et al. ............. 660/475 |
| 5,995,645 A | 11/1999 | Soenksen et al. ........... 382/133 |
| 6,021,344 A | 2/2000 | Lui et al. ................ 600/476 |
| 6,058,322 A | 5/2000 | Nishikawa et al. ......... 600/408 |
| 6,069,689 A | 5/2000 | Zeng et al. ............... 356/773 |
| 6,083,487 A | 7/2000 | Biel ...................... 424/9.6 |
| 6,091,985 A | 7/2000 | Alfano et al. ............ 600/476 |
| 6,095,982 A | 8/2000 | Richards-Kortum et al. ............. 600/476 |
| 6,096,065 A | 8/2000 | Crowley ................... 607/88 |
| 6,099,464 A | 8/2000 | Shimizu et al. ............ 600/104 |
| 6,104,945 A | 8/2000 | Modell et al. ............. 600/473 |
| 6,119,031 A | 9/2000 | Crowley ................... 600/407 |
| 6,124,597 A | 9/2000 | Shehada et al. ......... 250/461.2 |
| 6,146,897 A | 11/2000 | Cohenford et al. ............ 436/63 |
| 6,169,817 B1 | 1/2001 | Parker et al. ............. 382/131 |
| 6,187,289 B1 | 2/2001 | Richards-Kortum et al. . 424/9.8 |
| 6,208,887 B1 | 3/2001 | Clarke et al. ............. 600/476 |
| 6,241,662 B1 | 6/2001 | Richards-Kortum et al. ............. 600/310 |
| 6,243,601 B1 | 6/2001 | Wist ...................... 600/473 |
| 6,246,471 B1 | 6/2001 | Jung et al. ................. 356/73 |
| 6,246,479 B1 | 6/2001 | Jung et al. ................ 356/419 |
| 6,285,639 B1 | 9/2001 | Maenza et al. ............ 369/47.28 |
| 6,312,385 B1 | 11/2001 | Mo et al. ................. 600/443 |
| 6,317,617 B1 | 11/2001 | Gilhuijs et al. ........... 600/408 |
| D453,832 S | 2/2002 | Morrell et al. ............. D24/138 |
| D453,962 S | 2/2002 | Morrell et al. ............. D24/138 |
| D453,963 S | 2/2002 | Morrell et al. ............. D24/138 |
| D453,964 S | 2/2002 | Morrell et al. ............. D24/138 |
| 6,377,842 B1 | 4/2002 | Pogue et al. ............... 600/478 |
| 6,385,484 B2 | 5/2002 | Nordstrom et al. .......... 600/476 |
| 6,411,835 B1 | 6/2002 | Modell et al. ............. 600/407 |
| 6,411,838 B1 | 6/2002 | Nordstrom et al. .......... 600/476 |
| D460,821 S | 7/2002 | Morrell et al. ............. D24/138 |
| 6,421,553 B1 | 7/2002 | Costa et al. .............. 600/476 |
| 6,427,082 B1 | 7/2002 | Nordstrom et al. .......... 600/476 |
| 6,497,659 B1 * | 12/2002 | Rafert ..................... 600/331 |
| 6,571,118 B1 | 5/2003 | Utzinger et al. ........... 600/476 |
| 6,574,502 B2 | 6/2003 | Hayashi ................... 600/476 |
| 2001/0041843 A1 | 11/2001 | Modell et al. ............. 600/473 |
| 2002/0007123 A1 | 1/2002 | Balas et al. .............. 600/476 |
| 2002/0107668 A1 | 8/2002 | Costa et al. .............. 702/189 |
| 2002/0133073 A1 | 9/2002 | Nordstrom et al. .......... 600/426 |
| 2002/0197728 A1 | 12/2002 | Kaufman et al. ............ 436/164 |
| 2003/0207250 A1 | 11/2003 | Kaufman et al. ............... 435/4 |
| 2004/0007674 A1 | 1/2004 | Schomacker et al. ..... 250/458.1 |
| 2004/0010187 A1 | 1/2004 | Schomacker et al. ........ 600/317 |
| 2004/0010195 A1 | 1/2004 | Zelenchuk ................. 600/476 |

FOREIGN PATENT DOCUMENTS

| | | |
|---|---|---|
| EP | 0 641 542 | 3/1995 |
| EP | 0 689 045 | 12/1995 |
| EP | 0 737 849 A2 | 10/1996 |
| JP | 08-280602 | 10/1996 |
| SU | 1 223 092 | 4/1986 |
| WO | WO 92/19148 | 11/1992 |
| WO | 93/14688 | 8/1993 |
| WO | WO 94/26168 | 11/1994 |
| WO | WO 95/00067 | 1/1995 |
| WO | WO 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/41615 | 7/2000 |
| WO | WO 00/57361 | 9/2000 |
| WO | WO 00/59366 | 10/2000 |
| WO | WO 2004/005885 | 1/2004 |
| WO | WO 2004/005895 | 1/2004 |

OTHER PUBLICATIONS

Noble et al., "Automated, Nonrigid Alignment of Clinical Myocardial Contrast Echocardiography Image Sequences: Comparison with Manual Alignment," *Ultrasound in Medicine and Biology*, vol. 28, No. 1 (2002), pp. 115–123.

P. Davidovits et al. "Scanning Laser Microscope for Biological Investigations", Applied Optics, vol. 10, No. 7, pp. 1615–1619, Jul. 1971.

C.J.R. Sheppard et al. "Depth of Field in the Scanning Microscope", Optics Letters, vol. 3, No. 3, Sep. 1978, pp. 115–117.

C.J. Koester, "Scanning Mirror Microscope with Optical Sectioning Characteristics: Applications in Ophthalmology", Applied Optics, vol. 19, No. 11, Jun. 1980, pp. 1749–1757.

T. Wilson., "The Role of the Pinhold in Confocal Imaging Systems", Confocal Microscopy Handbook, pp. 99–113.

C. Koester, "Comparison of Optical Sectioning Methods: The Scanning Slit Confocal Microscope", Confocal Microscope Handbook, pp. 189–194.

Jeffrey W. Hall, et al. "Near–Infrared Spectrophotometry: A New Dimension in Clinical Chemistry", Clin. Chem 38/9, 1623–1631 (1992).

Kevin T. Schomacker, et al. "Ultraviolet Laser–Induced Fluorescence of Colonic Tissue; Basic Biology and Diagnostic Potential", Lasers in Surgery and Medicine, 12: 63–78, (1992).

S. Schwartz, "Real–time laser–scanning Confocal ratio imaging", American Laboratory, pp. 53–62 Apr. 1993.

R. Richards–Kortum et al. Description and Performance of a Fiber–optic Confocal Fluorescence Spectrometer, Applied Spectroscopy, vol. 48, No. 3 pp. 350–355. (1994).

J.M. Schmitt et al. "Interferometric Versus Confocal Techniques for Imaging Microstructures in Turbid Biological Media", Proc. SPIE, 2135 (1994), pp. 1–12.

N. Ramanujarn et al. Fluorescence Spectroscopy; A Diagnostic Tool for Cervical Intraepithelial Neoplasia (CIN), Gynecologic Oncology 52, pp. 31–38 (1994).

S.G. Anderson, "Confocal Laser Microscopes See A Wider Field of Application", Laser Focus World, pp. 83–86, Feb. 1994.

J.M. Schmitt et al. "Confocal Microscopy in Turbid Media", J. Opt. Soc. Am., vol. 11, pp. 2225–2235, Aug. 1994.

N. Ramanujarn et al. "In vivo diagnosis of cervical intraepithelial neoplasia using 337–nm–exited laser–induced fluorescence", Pro. Natl. Acad. Sci. USA, vol. 91, pp. 10193–10197, Oct. 1994.

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

Althof et al. (1997), "A rapid and automatic image registration algorithm with subpixel accuracy," *IEEE Transactions on Medical Imaging*, 16(3):308–316.

Aström et al. (1999), "Motion estimation in image sequences using the deformation of apparent contours," *IEEE Transactions on Pattern Analysis and Machine Intelligence*, 21(2):114–127.

Balakrishnama et al, "Linear Discriminant Analysis –A Brief Tutorial," *Institute for Signal and Information Processing Department of Electrical and Computer Engineering*, 8 pages.

Balas (1997), "An Imaging Colorimeter for Noncontact Tissue Color Mapping," *IEEE Transactions on Biomedical Engineering*, 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96–104.

Balas et al. (1997), "A modular diffuse reflection and fluorescence emission imaging colorimeter for the in–vivo study of parameters related with the phototoxic effect in PDT," *SPIE*, 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE*, vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology*, 53:153–157.

Bessey et al. (1949), "The Fluorometric measurement of the nucleotides of riboflavin and their concentration in tissues," *J. Biol.–Chem.*; 180:755–769.

Bors et al. (1998), "Optical flow estimation and moving object segmentation based on median radial basis function network," *IEEE Transactions on Image Processing*, 7(5):693–702.

Bouthemy et al. (1999), "A unified approach to shot change detection and camera motion characterization," *IEEE Transactions on Circuits and Systems for Video Technology*, 9(7):1030–1044.

Briachotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.*, 62:84R–101R.

Camus et al. (1997), "Real–time quantized optical flow," *Real–Time Imaging*, 3:71–86.

Caplier et al. (1998), "Real–time implementation of a MRF–based motion detection algorithm," *Real–Time Imaging*, 4:41–54.

Contini et al. (1989), "Colposcopy and Computer Graphics: a New Method?" *Amer. J. Obstet. Gynecol.*, 160(3):535–538.

Craine et al. (1993), "Digital Imaging Colposcopy: basic concepts and applications," *Amer. J. Obstet. Gynecol.*, 82(5):869–873.

Craine et al. (1998), "Digital imaging colposcopy: Corrected area measurements using shape–from–shading," *IEEE Transactions on Medical Imaging*, 17(6):1003–1010.

Crisp et al. (1990), "The Computerized Digital Imaging Colposcope: Future Directions," *Amer. J. Obstet. Gynecol.*, 162(6):1491–1497.

Cronjé et al. (1997), "Effects of Dilute Acetic Acid on the Cervical Smear," *Acta. Cytol.*, 41:1091–1094.

Dickman et al. (2001), "Identification of Cervical Neoplasia Using a Simulation of Human Vision," *Journal of Lower Genital Tract Disease*, 5(3):144–152.

Drezek et al. (1999), "Light scattering from cells: finite–difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.*, 182(5):1135–1139.

Dumontier et al. (1999), "Real–time DSP implementation for MRF–based video motion detection," *IEEE Transactions on Image Processing*, 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927–932.

Edebiri, A.A. (1990), "The relative significance of colposcopic discriptive appearances in the dianosis of cervical intraepithelial neoplasia," *Int. J. Gynecol. Obstet.*, 33:23–29.

Eisner et al. (1987), "Use of Cross–Correlation Function to Detect Patient Motion During Spectral Imaging," *Journal of Nuclear Medicine*, 28(1):97–101.

Ferris et al. (1998), "Colposcopy Quality Control: Establishing Colposcopy Criterion Standards for the NCI ALTS Trial Using Cervigrams," *J. Lower Genital Tract Disease*, 2(4):195–203.

Fleet et al. (1995), "Recursive Filters for Optical Flow," *IEEE Transactions on Pattern Analysis and Machine Intelligence*, 17(1):61–67.

Gao et al. (1998), "A work minimization approach to image morphing," *The Visual Computer*, 14:390–400.

Gauch (1999), "Image Segmentation and Analysis Via Multiscale Gradient Watershed Hierarchies," *IEEE Transactions on Image Processing*, 8(1):69–79.

Haralick (1984), "Digital Step Edges from Zero Crossing of Second Directional Derivatives," *IEEE Transactions on Pattern Analysis and Machine Intelligence*, 6(1):58–68.

Haris et al. (1998), "Hybrid Image Segmentation Using Watersheds and Fast Region Merging," *IEEE Transactions on Image Processing*, 7(12):1684–1699.

Helmerhorst et al. (1987), "The accuracy of colposcopically directed biopsy in diagnosis of CIN 2/3." *Eur. J. Obstet. Gyn. Reprod. Biol.*, 24, 221–229.

Horn et al. (1981), "Determining Optical Flow," *Artificial Intelligence*, 17(1–3):185–203.

Horn et al. (1993), "Determining Optical Flow": a retrospective, *Artificial Intelligence*, 59:81–87.

Huang et al. (1979), "A fast two–dimensional median filtering algorithm," *IEEE Transactions on Acoustics, Speech, and Signal Processing*, 27(1):13–18.

Jackway (1996), "Gradient Watersheds in Morphological Scale–Space," *IEEE Transactions on Image Processing*, 5(6):913–921.

Ji et al. (2000), "Texture Analysis for Classification of Cervix Lesions," *IEEE Transactions on Medical Imaging*, 19(11):1144–1149.

Kierkegaard et al. (1995), "Association between Colposcopic Findings and Histology in Cervical Lesions: The Significance of the Size of the Lesion" *Gynecologic Oncology*, 57:66–71.

Kumar et al. (1996), "Optical Flow: A Curve Evolution Approach," *IEEE Transactions on Image Processing*, 5(4):598–610.

Linde et al. (1980), An algorithm for vector quantizer design,: *IEEE Transactions on Communications*, 28(1):84–95.

MacAulay et al. (2002), "Variation of fluorescence spectroscopy during the menstrual cycle," *Optics Express*, 10(12):493–504.

MacLean A.B. (1999), "What is Acetowhite Epithelium," *Abstract Book: 10th World Congress of Cervical Pathology and Colposcopy*, Nov. 7–11, Buenos Aires, Argentina 41.

Marzetta et al. (1999), "A surprising radon transform result and its application to motion detection," *IEEE Transactions on Image Processing*, 8(8):1039–1049.

Miike et al. (1999), "Motion enhancement for preprocessing of optical flow and scientific visualization," *Pattern Recognition Letters*, 20:451–461.

Mikhail et al. (1995), "Computerized colposcopy and conservative management of cervical intraepithelial neoplasia in pregnancy," *Acta Obstet. Gynecol. Scand.*, 74:376–378.

Milanfar (1999), "Two–dimensional matched filtering for motion estimation," *IEEE Transactions on Image Processing*, 8(3):438–444.

Mitchell et al. (1998), "Colposcopy for the diagnosis of squamous intraepithelial lesions: a meta–analysis," *Obstet. Gynecol.*, 91(4):626–631.

Mycek et al. (1998), "Colonic polyp differentiation using time–resolved autofluorescence spectroscopy," *Gastrointestinal Endoscopy*, 48(4):390–394.

Nanda et al. (2000), "Accuracy of the Papanicolaou test in screening for and follow–up of cervical cytologic abnormalities: a systematic review," *Ann Intern Med.*, 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Noumeir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnosis and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164–171.

Schomacker et al. (1992), "Ultraviolet Laser–Induced Fluorescence of Colonic Polyps," *Gastroenterology*, 102:1155–1160.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences,"*IEEE Transactions on Medical Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and efficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transactions on Medical Imaging*, 16(5):630–641.

Wolberg et al. (1998) "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochastic relaxation," *IEEE Transactions on Signal Processing*, 40(2):310–322.

Zeng et al. (1993), "A computerized autofluorescence and diffuse reflectance spectroanalyser system for *in vivo* skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy*, 52(6):833–839.

\* cited by examiner

OPTICAL PROBE ACCESSORY DEVICE FOR USE IN VIVO DIAGNOSTIC PROCEDURES

RELATED APPLICATIONS

The application claims priority to U.S. Provisional Application Serial No. 60/138,235, filed on Jun. 9, 1999 and is also a continuation-in part of U.S. patent application Ser. No. 09/481,762, filed Jan. 11, 2000, which claims priority to U.S. Provisional Application Serial No. 60/115,373, filed Jan. 11, 1999, and is a continuation-in-part of U.S. patent application Ser. No. 09/241,806, filed Feb. 2, 1999, now U.S. Pat. No. 6,411,835 which is a continuation-in-part of U.S. patent application Ser. No. 08/782,936, filed Jan. 13, 1997 now U.S. Pat. No. 6,104,945. The entirety of these applications is incorporated by reference.

FIELD OF THE INVENTION

The invention relates to an accessory device for an optical probe for use in in vivo diagnostic procedures. The accessory device provides an optimal optical path for light from an optical probe while minimizing patient discomfort. The accessory device features optional selectable elements to enhance its versatility in in vivo diagnostic procedures.

BACKGROUND OF THE INVENTION

The early detection of disease increases the chance for successful therapeutic intervention. Non-invasive optical diagnostic devices which detect changes in the biochemical and structural features of tissues provide tools to detect the early stages of disease (e.g., cancer). An optical device for detecting tissue features typically comprises a console unit which includes a light source, a detector, electronics, and a computer, in communication with an optical probe through which light is transmitted to and from a tissue. The optical probe can be the end of a fiber optic cable or can contain complex optical elements intended to shape an output light beam from an optical source into a desired geometry.

Optical probes coupled to endoscopic devices have been used to obtain tissue-specific information from patients. Representative organs which can be characterized using an endoscopic approach include the colon, uterus, bladder, and stomach. Fluorescence spectroscopy using endoscopic optical probes can distinguish between cancerous and precancerous tissue in these organs. However, the development of optical probes for clinical use has been hampered due to the difficulty of miniaturizing the optical elements necessary for the collection of optical data. Additional constraints arise because an optical probe, like any medical access device, must be decontaminated and sterilized prior to reuse. The delicate construction of light directing and focussing elements within the optical probe generally make it difficult, if not impossible, to sterilize the probe.

Because it is generally not economical to discard an optical probe after a single use, it is desirable to provide an accessory device which acts as a shield between the illumination optics of the optical probe and the tissue being analyzed. While it is generally known in the art to equip a medical device with a protective barrier or sheath to provide a cover for the device, it is desirable to provide an accessory device for an optical probe which serves more than a mere barrier function, but which complements the function of the optical probe. Accordingly, the present invention provides an accessory device for an optical probe which comprises multiple optional features to enhance the versatility of the device in in vivo diagnostic procedures.

SUMMARY OF THE INVENTION

The invention recognizes that optical probes function both as medical access devices and as instruments which collect complex optical data. The invention provides an optical probe accessory device which accesses luminal spaces within the body of a patient without sacrificing the quality of optical data obtained. The accessory device further comprises either, singly, or in combination, selectable features which optimize light transmission, maximize patient comfort, and provide single-use capabilities.

In one aspect of the invention, an accessory device for an optical probe is provided which creates an optimal light path between the optical probe and a target tissue. Optional optical elements are provided which enhance the light transmitting and light receiving functions of the probe. In one embodiment, an accessory device comprises optical elements which create an optical waveguide to improve optical data collection by the probe. In this embodiment, the accessory device includes a window which functions as an objective for the optical probe's illumination elements. In other embodiments of the invention, the window is coated with anti-fog and/or anti-glare agents to maximize the passage of diagnostic light to and from the probe. In still other embodiments, the accessory device is adapted to function with an optical probe which comprises a plurality of optical fibers and the accessory device comprises a plurality of openings sized to accept a plurality of light transmitting fibers from the optical probe.

By acting as an intermediate between the optical probe and the target tissue being analyzed, the accessory device is not subject to the same design constraints as the optical probe (i.e., does not have to be a certain minimum size to accommodate a plurality of optical elements). Accordingly, in one aspect of the invention, the accessory device can be tailored to conform to a particular body lumen being accessed (e.g., in one embodiment, the cervix, in another embodiment, an ear canal).

For example, an optical probe accessory device which comprises, at least in portion, a flexible material which conforms to the shape of a body space being accessed is contemplated by the present invention. The flexible portion provides a shield between the tissue being assayed by the optical probe and the probe itself. In another embodiment, a segment of the flexible portion conforms to an end of the optical probe bearing illumination optics, protecting the illumination optics of the probe from bodily fluids while shielding the patient from contaminants. In still another embodiment, the flexible nature of the accessory device allows it to be rolled up before and after use with the probe.

In another aspect of the invention, the attachment device is a single-use, disposable device, allowing the optical probe to be used multiple times without transmitting disease from one patient to another. In this embodiment, to maximize the attachment device's capacity to protect patients from contamination, the attachment device is crippled, either mechanically, or electronically, after a single use, so that an optical probe will not function with an attachment device which has been previously used.

For example, the accessory device comprises a body and an attachment element and is mechanically prevented from re-use. In this embodiment, the attachment element attaches the accessory device to the probe and detaches from the body of the accessory device when the accessory device is removed from the probe. The accessory device is unable to function without the attachment element and so detachment of the accessory device from the probe prevents its reuse. In one embodiment, the attachment element comprises a grasping element, such as a tab or a snap ring which detaches the attachment element from the body of the accessory device. In a further embodiment, the attachment element is separated from the body of the accessory device by perforations and rupturing the perforations detaches the attachment element from the body of the accessory device.

In yet another embodiment, a disposable, single-use accessory device for an optical probe comprises an electrical element rather than a mechanical element which prevents its re-use in another patient. In one embodiment, the accessory device comprises an electrical element bearing encoded information (e.g., identification information). In another embodiment, the electrical element is remotely programmable and the information contained within the electrical element can be altered by the user.

In a further aspect of the present invention, a system is provided which comprises a processor and an electrical element reader. The electrical element reader accesses information encoded in the electrical element carried by the accessory device and transmits a signal to the processor relating to identification information carried by the electrical element. The processor includes a memory which stores identification information and which compares the stored information with identification information encoded by the electrical element. The processor transmits instructions based on whether or not a match is found between identification information encoded in the electrical element and identification information stored within the memory. If no match is found, the identification information encoded in the electrical element is added to the memory.

The instructions transmitted by the processor control the actuation of the optical probe. For example, in one embodiment, the system includes a light source in communication with both the processor and the optical probe. Transmission of light from the light source to the probe relies upon instructions received from the processor. In another embodiment, instructions from the processor can include particular operating parameters relating to a tissue-specific diagnostic procedure (for example, but not limited to the diagnosis of cervical cancer). Use of an accessory device with an electrical element which identifies the device as one which is suited for accessing the cervix triggers the processor to implement operating parameters suited to the diagnosis of cervical cancer. Thus, the system provides flexibility that allows the optical probe to be used with a variety of accessory devices in a variety of diagnostic procedures.

Any or all of the foregoing optional features (the optical features to enhance light transmission, minimally invasive, tissue-conforming structural features, mechanical or electrical disabling elements conferring single-use capabilities) can be combined to meet the needs of a particular diagnostic procedure. Because of the modular nature of the optical probe accessory device, the optical probe itself is not limited for use in a single diagnostic application but can be adapted for a variety of diagnostic applications.

The foregoing and other objects, aspects, features, and advantages of the invention will become apparent from the following description and from the claims.

BRIEF DESCRIPTION OF THE DRAWINGS

The objects and features of the invention can be better understood with reference to the following detailed description and accompanying drawings, in which like reference characters generally refer to the same parts throughout the different views.

FIG. 2A shows a side view of such a device. FIG. 2B shows a top view.

FIG. 6A shows an accessory device comprising a bar code on the side of the device. FIGS. 6B and C show an embodiment of the invention in which the bar code is placed on an optical window which forms the end of the device distal to the illumination optics of the optical probe. FIG. 6A shows a view of the end of the device bearing the bar code. FIG. 6C shows a view of the side of the device.

DETAILED DESCRIPTION

Figure 1:
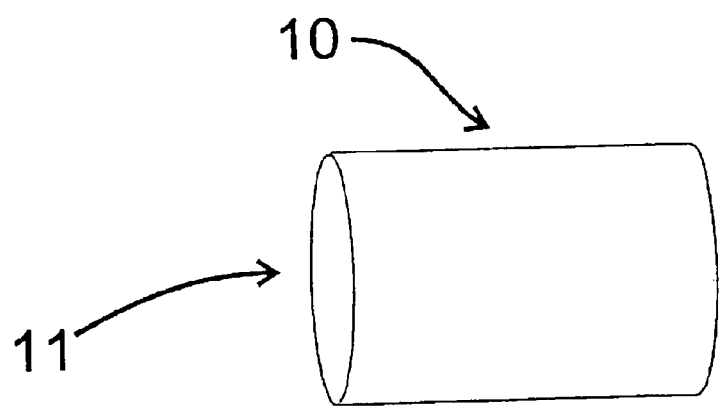
FIG. 1 shows a schematic representation of an accessory device for an optical probe according to one embodiment comprising an optical window located at an end of the device distal from the illumination optics of an optical probe.

Because an accessory device according to the invention complements the function of an optical probe such accessory devices provide more than merely a sheath for an optical probe. An accessory device of the invention comprises a number of optional features which a user can select in optimizing the accessory device to suit a particular application. Any or all of these options can be present in an accessory device according to the invention. Because of the many permutations of accessory devices which can be designed according to the invention, the optical probe itself acquires more versatility and can be used in a variety of diagnostic settings. It will be apparent to those of skill in the art after reading this disclosure that other options can additionally be provided, and such options are encompassed within the scope of the invention. All that is required to practice the present invention, is that the accessory device permit optical data collection by an optical probe without obstruction. A number of preferred features of a device of the invention is discussed below. These may be used singly or in combination with each other or with other probe features known in the art. The skilled artisan appreciates that numerous other features may be included in a device of the invention, either alone or in combination.

Option 1. Maximal Light Transmission

In one aspect of the invention, the accessory device provides additional optical features to enhance the transmission of light from the optical probe to the tissue and from the tissue to the optical probe. According to this aspect of the invention, the user selects optical features that are for the accessory device that are compatible with the operation parameters of the optical probe.

In practice, the accessory device is fabricated using material which has a high optical transmission over the spectral bandwidth of operation of the probe. For example, for some probes, obtaining an image by the probe is not as important as obtaining a very high signal-to-noise ratio from an optical response in spectral regions that do not overlap, or only partially overlap, the visible region of the spectrum. That is, the inclusion of features to ensure adequate performance of the optics to create a visual image of the sample may degrade the performance of the device in collecting acceptable optical signals such as fluorescence, Raman, or reflectance spectra. In embodiments where image quality is not an issue, the portion of the accessory device actually transmitting an ultraviolet (UV) excitation beam (e.g., the end of the device distal to the probe) can be made of a very thin Teflon® or can comprise other fluoroplastics such as THV-200P® (a TFE/HPF/VDF terfluoropolymer from the 3M® corporation). These plastics do not demonstrate a significant fluorescent response when irradiated with UV.

In some embodiments, the accessory device is used with an optical probe which functions by directing light to a tissue and receiving at least fluorescent light re-emitted from the tissue after absorption of the excitation light, while in other embodiments, the accessory device receives scattered light from a target tissue, such as elastic scattered light (e.g. reflectance spectroscopy) or inelastic scattered light (e.g., as in Raman spectroscopy applications). In these embodiments, the light being directed back to the probe provides diagnostic information relating to the chemical/structural features of a tissue being analyzed rather than its morphological features. An accessory device used in these applications is made of materials which provide minimal interference with the light being directed back towards the probe. In a preferred embodiment, the accessory device comprises a low-fluorescing plastic and has high optical transmission through the ultraviolet and visible spectral regions from 300 nm to 750 nm.

In other embodiments, where imaging is a function of the probe, an accessory device is provided which does not fluoresce when illuminated by a laser or other light source and has a sufficiently large aperture or opening to collect low levels of light emitted during fluorescence of some samples such as tissue, good modulation transfer function for good image transmission, and/or a lack of color tint to preserve spectral accuracy. The accessory device can be fabricated from material including, but not limited to, UVT acrylic or amorphous polyolefin (e.g., Zeonex®, Nippon Zeon CO., Ltd.) and the like. The skilled artisan can recognize and identify equivalent materials using routine experimentation and routine testing.

The type of optical probe, and hence the type of accessory device used, will depend upon the particular diagnostic application required. For example, in diagnosing cervical tissue pathologies, in some instances it is desirable to obtain both imaging and non-imaging optical information. This combination of modalities is important when spatial location of biopsy sites is the output of the optical device. In this embodiment, an accessory device should be selected which creates minimal interference with the spectroscopic functions of the device, and has good imaging capability to locate specific tissue sites. However, when the application is ASCUS Triage (Atypical Squamous Cells of Undetermined Significance Triage), non-imaging information is more important, because determining the location of the abnormal tissue is not necessary. Here, an accessory device can be used which is not suited for imaging purposes. In a third instance, the optical probe can be used as an adjunct to a standard pap smear test. In this embodiment, a non-imaging device is suitable.

Figures 2A, 2B:
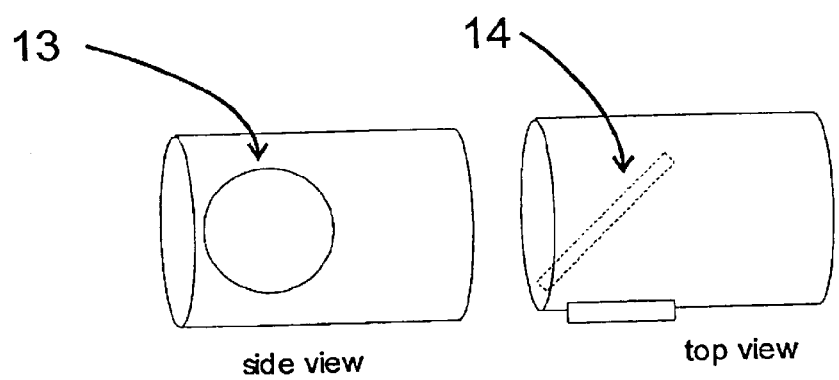
FIGS. 2A and 2B show a schematic representation of an accessory device according to one embodiment comprising a single side-looking window.
Figure 3:
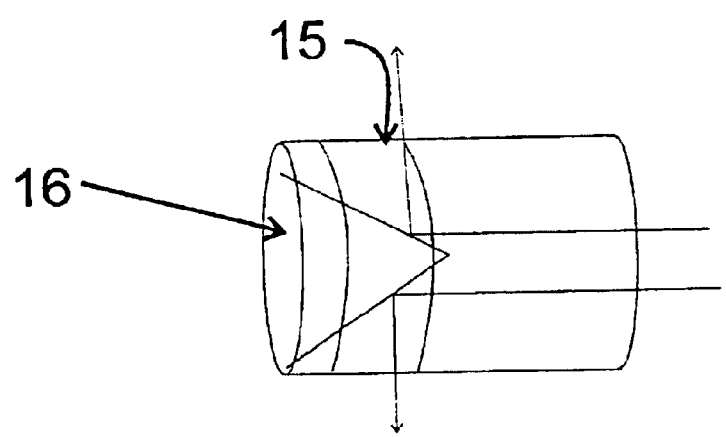
FIG. 3 shows a schematic representation of a single use accessory probe according to one embodiment comprising a sectional transparent window.

The present invention also contemplates that the optical features of the accessory device include optical elements which complement the function of the optical probe. In one embodiment, the accessory device includes a flat window which permits passage of diagnostic light to and from the optical probe without distortion. Window materials include, but are not limited to, cast or molded polymethylmetacrylate (PMMA) and other materials which provide no significant fluorescence in response to an excitation beam. By way on non-limiting examples, polystyrene or polycarbonate are two such materials. The placement of the window on the accessory device is selected to optimize the collection of light from a tissue being analyzed. In one embodiment, shown in FIG. 1, the window 11 is at the end of the accessory body 10 most distal from the probe. In another preferred embodiment, shown in FIGS. 2A-B and FIG. 3, the window is provided on the side of the accessory device, giving the opportunity to gather optical information from the side as the device is moved along or through a sample. The window can be configured in a variety of shapes. In the embodiment shown in FIGS. 2A and 2B, the accessory device comprises a circular window 13. In the embodiment shown in FIG. 3, the window is a transparent section 15 of the accessory device.

In another preferred device, the window is fastened onto the end of a cylindrical- or toroidal-shaped ring segment that is press-fitted onto the accessory device, forming an annular lens which functions as an objective for the optical probe's illumination elements. The wall thickness of the ring segment on which the window/lens sits is designed to allow the accessory device to act as an optical waveguide to direct light onto target tissues for better visualization or data collection. In one embodiment of the invention, the wall thickness of the ring segment is between about 0.5 mm and 2.0 mm. The window itself can form a lens, or alternatively, a lens can be added to the window as a separate element. For example, the window can be segmented so that a portion of the structure is flat (i.e., optically passive), while other portions are curved (i.e., forming lens segments).

In another accessory device contemplated by the invention, a delivery apparatus is operably connected to the window for dispensing a fluid which has an index of refraction matching the window or other exposed optical elements in the accessory device and/or optical probe. Delivery devices encompassed within the scope of the invention include a bead or other container residing in a space defined by the ring segment which can be caused to break and discharge its fluid. Fluid from the delivery device spreads downward by capillary force to fill the space between optical elements in the accessory device (e.g., such as the window itself) and the optical probe. In another embodiment, the window is coated with an anti-fog agent or an anti-glare agent. In still a further embodiment, the accessory device is provided with a flexible sleeve which covers the window and serves a protective function.

The accessory device of the present invention can also be adapted to include other optical elements to facilitate the acquisition of diagnostic data, such as filters, polarizers, or light reflecting elements. For example, in one embodiment of the invention, the distal end of the accessory device includes a reflecting element such as an integral faceted mirror. In a further embodiment, the reflecting element is in the shape of a cone which has a half angle of 45 degrees. A light beam impinging on one of the facets of the reflecting element will be reflected at a 90 degree angle to the incident light causing it to be emitted laterally from the distal end of the accessory device, allowing light to be efficiently directed to the target tissue within the lumen the accessory device is accessing. A light-focusing element can additionally be provided in optical communication with the reflecting element in order to focus light beams appropriately on the target tissue. In still further embodiments of the invention, reflecting elements are provided within the body of the accessory device in optical communication with a window. In the embodiment of the invention shown in FIG. 2B, the reflective element is a reflective planar surface 14. In the embodiment of the invention shown in FIG. 3, the reflecting element is a conical surface which directs light from the optical probe towards the transparent sectional window 15. It should be apparent to those a skill in the art that a variety of shapes of reflecting surfaces can be provided and positioned to optimize the light path from the optical probe to the window of the accessory device.

In embodiments of the invention where the optical probe being used with the accessory device comprises a plurality of optical fibers, a reflecting element can be provided whose number of facets correspond to the number of excitation fibers in the probe, creating an optimal light path between the target tissue and light from the optical probe through the accessory device. In this embodiment, the accessory device can also be configured to attach to the probe in way that further optimizes this light path. For example, in one preferred embodiment, the accessory device is fitted onto the probe via a connecting ring which comprises openings designed to adapt to a particular configuration of optical fibers (e.g., bundled or spaced). Attachment of the probe to the accessory device can only be achieved by correctly aligning optical fibers with appropriate regions in the accessory device. In one instance, the optical probe comprises a plurality of pins which fit into holes in the connecting ring of the accessory device only when the accessory device is positioned in a specific orientation, ensuring the proper orientation of the optical probe with respect to the accessory device.

Additionally, the accessory device can be adapted to provide a light source for evenly illuminating a tissue being visualized. In one embodiment, the accessory device includes an illuminating light source positioned around the circumference of the accessory device. The illuminating light source can be an integral part of the device or can be snapped on by a ring mechanism.

In applications where visible marking or tagging specific regions of the sample is necessary or important, the accessory device is provided with a dispenser capable of directing a marking fluid toward the sample. The fluid can be applied to localized regions of the sample for identifying selected regions, or it can be dispensed over a broad region of the sample, as a bath or wash. The purpose of the bath or wash may be to affect chemical changes in the sample to aid in the identification of substances in or characteristics of the sample. For example, in optical detection of precancerous lesions of the cervix, the application of a mild acetic acid wash increases the contrast and visibility of the regions of suspicious lesions.

Other types of fluids that can be used to enhance visualization of the sample, include hypertonic, hypotonic, hyperosmotic, and hypo-osmotic solutions. Hyper- or hypo-osmotic solutions can be generated in a number of ways, such as by using distilled water, either alone, or in combination with ionic or nonionic molecular constituents. Varying the hydrogen ion concentration of a fluid (e.g., pH) can generate additional visualization-enhancing agents. Dye solutions can also be applied such as, for example, Lugol's iodine, toluidine blue or methylene blue, and others.

Option 2. Minimal Invasiveness, Tissue-Conforming Structure

The accessory device can be designed to conform to a particular lumen being accessed, thus minimizing the invasive effect of the accessory device. In one embodiment, the accessory device comprises a flexible portion which provides a shield between the tissue being assayed and the optical probe while at the same time maximizing patient comfort by adapting itself to any space being accessed by the device. In one embodiment, the flexible accessory device can be in the form of an inflatable balloon into which a fluid (e.g., an index-matching fluid)is inserted to partially inflate the structure. Balloons can be made from compliant materials, such as polyethylene, latex (natural or synthetic), polyurethane, and silicone, or non-compliant materials, such as polyethylene terephthalate (PET).

When brought into contact with the tissue, the flexible accessory device distributes the contact pressure of the device evenly over the entire contact surface (such as a body lumen), while the index-matching fluid provides good optical communication with the tissue. In another embodiment, the flexible portion also conforms to the end of the optical probe bearing illumination optics, shielding the illumination optics of the probe from body fluids, while simultaneously shielding the patient from contamination by the probe. In this embodiment of the invention, the accessory device comprises, at least in portion, a shrink-fitted material (e.g., which can be shrunk using heat). A heating element (such as, but not limited to, a resister) can be included in the shrink-fitted material such that shrinkage is triggered when a voltage is applied to the resistor. Alternatively, the material can be shrunk using a heating device such as a hand-held hairdryer. Because of the flexible nature of the accessory device, it can be packaged in a rolled-up state (e.g., in a sterile wrapper) to be unrolled over the optical probe when it is ready to be used.

In one embodiment, the accessory device comprises both a flexible portion and a rigid tip portion. The length and diameter of the tip portion is selected to be optimal for accessing a particular body lumen and to provide for the effective transmission of diagnostic light from the optical probe, while the flexible portion of the accessory device is conformed like a skirt and is proximal to the end of the optical probe bearing illumination optics. The flared and flexible nature of the flexible portion minimizes patient discomfort from the entry of any portion of the optical probe itself into the body cavity being accessed. The flexible material and the rigid portion of the accessory device can be molded as a single unit or can be molded separately and connected together The optical probe accessory device according to the present invention can also be designed for a particular anatomic application, e.g., for obtaining information relating to tissue features of the gastrointestinal tract, the urinary tract, the peritoneal cavity, the thorax, ear canal, and the female reproductive tract. Other organs suitable for endoscopic or percutaneous access will be apparent to those of ordinary skill in the art. In each of these cases, the accessory device is designed as a probe with a particular geometry adapted for the body region towards which it is directed. In one embodiment of the invention, an accessory device is provided for use with an optical probe used in the cervix. In this embodiment, the accessory device covers the sides of the probe that encounters the vaginal walls and additionally covers the end of the optical probe comprising illumination optics. In a further embodiment, the accessory device is designed to at least partially cover an optical probe and is capable of passing, with the probe, through a distal aperture of an endoscope. In this embodiment, the accessory device is accordingly limited in sized to conform to the dimensions of the body cavity being accessed and the dimensions of the endoscope.

In still other embodiments of the invention, the accessory device is designed to transmit light from an optical probe to the surface of a tissue which is not accessed through a lumen, for example, the skin, or breast tissue, or tissue within an open surgical field.

Option 3. Single-Use Device

In accordance with the present invention, a single-use accessory device is provided for at least partially covering an optical probe. In one embodiment, the accessory device entirely covers the probe, while in another embodiment, the accessory device covers or shield those parts of the probe adapted for contact with a body tissue of a patient. As defined herein, the term "single-use" is understood to mean that the use of the accessory device is restricted to use with a single patient. However, in some embodiments, use can be confined to a single diagnostic measurement.

Figure 4:
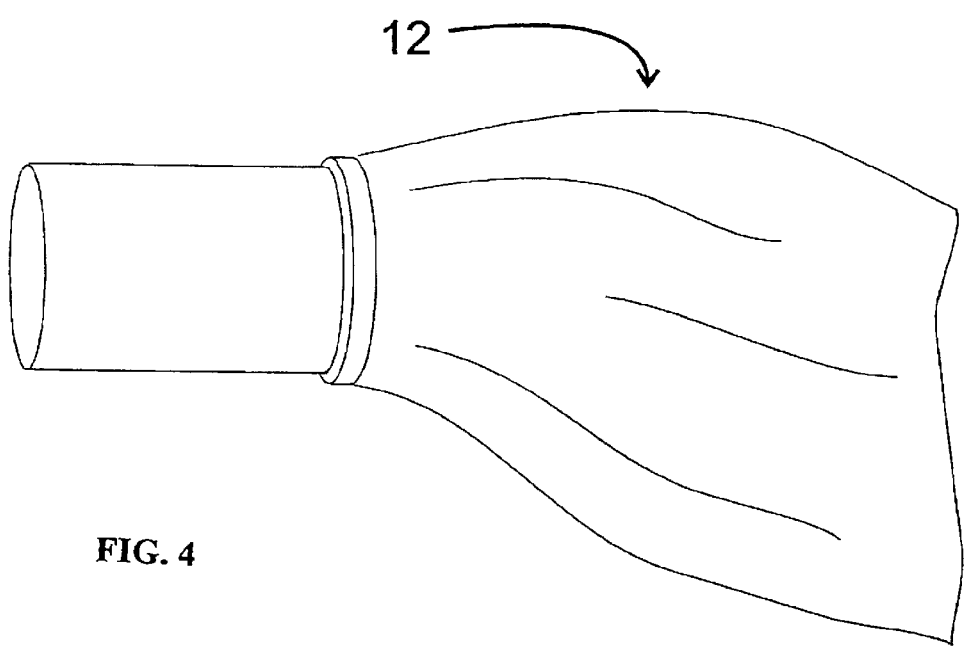
FIG. 4 shows a schematic representation of a single-use accessory device according to one embodiment comprising a flexible tear-away sheath.

In one preferred embodiment according to this aspect of the invention, the accessory device comprises both a body and an attachment element for attaching the accessory device to the probe wherein the device is mechanically prevented from re-use. For example, the accessory device comprises a breakable element to allow for physical breakage of at least a portion of the device upon removal from the optical probe. The attachment element according to this embodiment includes at least one breakable portion which must be broken in order to remove the accessory device from the probe. Breaking the breakable portion cripples the accessory device, preventing its reattachment and re-use. In another embodiment, the breakable portion includes a grasping element, such as a tab or snap ring, and grasping the grasping element results in breaking the body of the accessory device from the attachment element. In still another embodiment, as shown in FIG. 4, the attachment element comprises a flexible material 12 and the accessory device can only be detached from the probe by tearing the flexible material 12, separating the attachment element portion of the accessory device from the body portion. Alternatively, the flexible element can comprise a weakened material, or breakpoint, where it joins to the body of the device (e.g., perforations) to facilitate tearing. The breakpoint is more susceptible to mechanical stress than the remaining portions of the device.

The attachment element can be mechanically attached to optical probe by a variety of mechanisms, including, but not limited, to a tab/slot mechanism (such as a tab on the attachment element fits into a slot on the outside of the optical probe or visa versa), a magnetic attachment means, a lock and pin mechanism, a band-latching mechanism, or a string. Other types of attachment mechanisms (such as fasteners, elastic bands, strings within the accessory device which can hook onto the probe, Velcro, adhesive, tapes, glues), including those which rely on mating a protruding element (on the accessory device or the probe) to a recessed element (on the probe or the accessory device) will doubtless be apparent to those of skill in the art, and are included within the scope of the invention.

In another embodiment, the actual means of attachment of the attachment element is the breakable element in the device. For example, in one embodiment, where the attachment element attaches to the probe by a tab/slot mechanism, removal of the accessory device can only be performed by breaking the tab off, thereby preventing the accessory device from being reattached. In another embodiment, where a protruding mating element is provided on the accessory device to allow it to mate with a recessed element in the optical probe, the protruding mating element is designed to tear along a tear line, or perforation, in the accessory device upon mechanical stress (e.g., when the protruding element on the attachment element is disengaged from recessed element on the surface of the optical probe), preventing the protruding mating element from functioning in future.

In yet another embodiment of the invention, at least the attachment element of the device is made of a flexible material and a "cinch purse" string is provided to both secure the attachment element to the device and to provide a grasping element. In this embodiment, the string is attached to a breakable element so that pulling the string breaks the breakable element and permits the flexible portion of the accessory device to be rolled over, away from the optical probe. Once the breakable element is broken, the accessory device is unable to be reattached to the optical probe.

While the attachment element can attach directly to the optical probe, it can also attach through an intermediate interfacing element which itself attaches to the probe (e.g., via a ring or a plastic connecting sleeve). In a further embodiment of the invention, the attachment element and the body of the accessory device are modules which can be fitted together. Different types of interfacing elements can be used to interface different types of attachment elements and bodies to different optical probes, allowing the user to select and combine different desired features of the accessory device with a particular kind of optical probe.

In another embodiment of the single-use option, the accessory device is prevented from reuse by degrading the optical quality of the accessory device after use. For example, coatings susceptible to ultraviolet radiation, can be placed on the light-transmitting portion of the accessory device. During proper use of the device, the coating is subjected to a sufficient quantity of ultraviolet radiation so that it becomes at least partially opaque, preventing its reuse.

The invention also provides an accessory device which can be disabled after use without physically altering the device, that is, electronically, for example. In one embodiment, an electrical contact between the accessory and the optical probe is provided. In this embodiment, an electrical element is embedded within the accessory device which is capable of making electrical contact with the optical probe when the accessory device is properly affixed to the probe. As defined herein, the term "electrical element" encompasses both passive electrical elements (e.g., resistors, capacitors, inductors, diodes, and others) and active electrical elements (e.g., transistors, integrated circuits, such as microchips, and others). In one embodiment, after use, the optical probe delivers a current to the accessory device sufficient to destroy the electrical element, thus preventing reuse of the accessory device.

Figure 5:
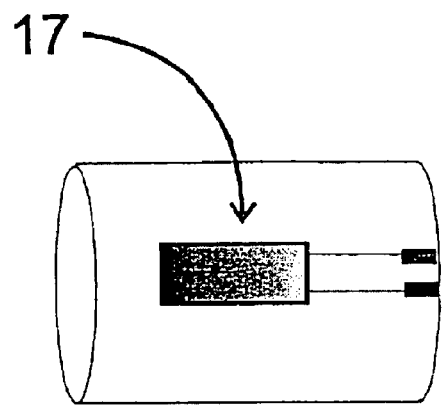
FIG. 5 shows a single-use accessory device according to one embodiment of the invention comprising an electrical element for encoding identification information.

In another embodiment, as shown in FIG. 5, the accessory device is provided with an electrical element 17 bearing encoded information. The electrical element can be secured to the accessory device by insertion at a notch on the surface of the device, or alternatively, can be held in place by a biocompatible adhesive (e.g., a cyanoacrylic adhesive) and can additionally include electrical contact elements for making contact with the probe.

In one embodiment of the invention, the electrical element 17 bears encoded information relating to the identification of the accessory device. For example, the encoded information identifies the device as one which has already been used with the optical probe. In a further embodiment, the electrical element 17 includes encoded information relating a target tissue which is being analyzed. Additional information encoded by the electrical element 17 includes, but is not limited to, time, present date, date of manufacture, materials used in construction, and the condition of the optical probe or the processing system used with the optical probe. Additionally, the electrical element 17 can include information regarding the intended use of the optical probe, and can enable only certain modes of operation of the probe. As defined herein, an "operating mode" refers to either, or both, the input or output of the optical probe. In one embodiment, the operating mode is a functioning or non-functioning state of the optical probe. In another embodiment, the operating mode is any of a plurality of input or output states of the device. For example, in one operating mode, the optical probe is directed to provide optical information relating to the location of a sample (e.g., a cancerous tissue) while in another operating mode, the optical probe is directed to provide information relating only to a biochemical feature of a sample (e.g., the presence or absence of fluorescence relating to a cancerous or precancerous state), while in still another operating mode, both types of information are provided.

Different types of electrical elements can be used. The electrical element can be a programmable read-only memory chip (PROM). The electrical element can be remotely programmable. In another embodiment of the invention, the electrical element is an RFID (radiofrequency identification device) or another active semiconductor device.

Information within the electrical element can be passed on to a processor in communication with the optical probe through a electrical element reader which accesses stored information in the electrical element in a non-contacting manner. In one embodiment, the electrical element reader is capable of receiving electromagnetic signals. In another embodiment, the electrical element reader is capable of receiving radiosignals from the electrical element.

When the electrical element reader is placed in a location in which it can access stored identification information encoded in the electrical element, the electrical element reader transfers this information to a processor to which the optical probe is operatively connected. For example, the electrical element reader can be either attachable to the optical probe or an integral part of the optical probe itself, such that the reader has access to the electrical element as soon as the accessory device is attached to the optical probe. Information from the electrical element is thus immediately transferred to the processor which provides instructions to the probe to either enable it or prevent it from functioning. In one embodiment, where the electrical element is an RFID chip, the "reader" is a transponder for receiving radiosignals from the electrical element.

In some applications, it is desirable to re-use the accessory device if another diagnostic test needs to be done with the same patient within a short time of the first diagnostic test (e.g., where the probe has not been removed from the patient). In this embodiment, the electrical element can be re-programmed or programmed with additional information, allowing the optical probe to function with the same accessory device. In certain embodiments of the invention, the electrical element reader is configured as an encoding device to conveniently change or add information stored within the electrical element.

As contemplated herein, processor includes a memory which comprises identification information identifying accessory devices that have been used with the optical probe. If a match is found between the identification information obtained by the electrical element reader and the identification information within the memory, the processor transmits instructions to the optical probe which prevents it from functioning. The instructions are then relayed to component(s) of an optical diagnostic system of which the optical probe is a part. For example, the optical diagnostic system comprises a light source which is in optical communication with the optical probe. The presence of a match between identification information encoded by the electrical element and identification information within the memory of the processor prevents light from being transmitted from the light source to the optical probe. In another embodiment of the invention, the optical diagnostic system comprises an optical probe-locking device which prevents the probe from being moved (e.g., to position it within a patient) if a match is found thus effectively preventing the probe from being used with the "wrong" accessory device. When no match is found between the information stored within the electrical element and information stored within the memory, the identification information relating to the electrical element is added to the memory. In this way, subsequent use of the accessory device will result in instructions being sent to the probe which prevents it from operating.

In an alternative embodiment, the processor can transmit instructions to the optical probe which allow it to function if a "correct" accessory device is used with the probe. In this embodiment, the processor transmits instructions to either the probe itself and/or to other components of the optical diagnostic system when no match is found between identification information encoded in the electrical element and the identification information stored in the memory. The instructions then trigger the optical probe or other component of the optical diagnostic system to function (for example, light can be transmitted through the optical probe or a specific diagnostic application can be run in response to the instructions).

In another embodiment, the electrical element is encoded with identification information which can only be read if the accessory device is positioned in a correct orientation with respect to the optical probe (for example, in an orientation which maximizes light transmission from the probe to the accessory device). In this embodiment, the processor will only transmit instructions to the optical probe to allow the probe to function if the accessory device is positioned correctly.

Information other than identifying information can also be transmitted to the processor via the electrical element. For example, information relating to the "readiness" of the optical probe/accessory device can be provided to the electrical element by sensors on the accessory device or the optical probe which are responsive to the environment in which the accessory device/and or probe is placed. The electrical element in turn transmits the information to the processor which can alter the functioning of the probe as appropriate.

The electrical element can further include information relating to the target tissue being analyzed. In this embodiment of the invention, information read by the electrical element reader triggers the processor to activate diagnostic programs unique to the analysis of that particular tissue. For example, the accessory device comprises a electrical element identifying it as an accessory device used to access the cervix. When the processor receives this information from the electrical element reader, the processor will access specific computer program product(s) (e.g., software applications) relating to the diagnosis of cervical tissue pathologies (e.g., cervical cancer) and will activate particular data input or data display screens that relate to diagnosing these pathologies. In other embodiments, the electrical element can include patient identifying information, including information relating to a history of a particular disease (e.g., whether the patient has a family history of cervical cancer).

In certain embodiments, a particular type of accessory device is preferred for a particular diagnostic application. In these embodiments, it is desirable to prevent an optical diagnostic system from functioning unless it is used with a suitable accessory device. In order to ensure that the proper accessory device is used in its appropriate diagnostic application, the electrical element in the accessory device is encoded with information indicating that it is suited for a particular use(s). When the processor accesses this information through the electrical element reader, only a proper match between the use and the device will permit the optical probe or other components of the optical system to function.

Although, non-physical means of crippling the accessory device after a single use have been disclosed with reference to an electrical element, it should be apparent to those of skill in the art that a number of different types of feedback mechanisms can be incorporated into an optical diagnostic system. In one embodiment, an optical probe is provided which is equipped with a light emitting diode and an infrared sensor, while the accessory device is marked with a series of lines on one of its surfaces providing identification information. In this embodiment, the optical probe sensor obtains information relating to the accessory device's identification information and transfers this information to the processor which sends instructions to the probe or other components of the system to enable or prevent the probe from functioning with that particular accessory device.

Figure 6A:
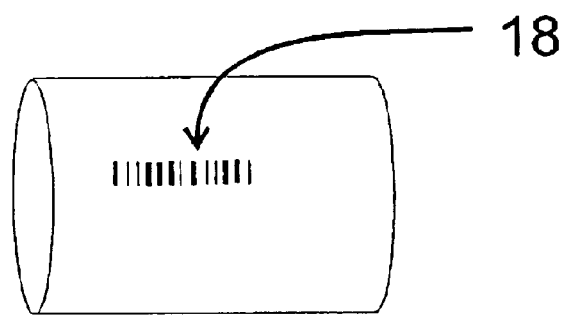
FIGS. 6A-C show schematic representations of accessory devices for optical probes marked with identifying information in the form of a bar code.
Figure 6B:
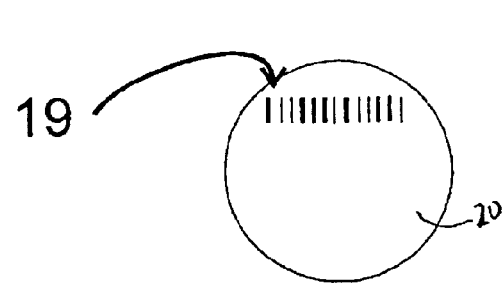
Figure 6C:
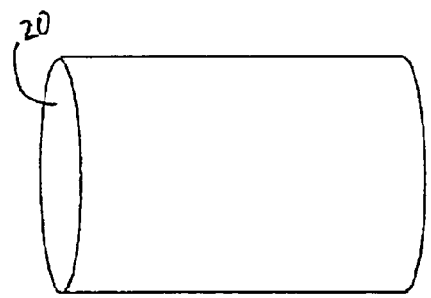

Optical methods for communicating the usage history of the accessory device to the optical probe can also include bar codes. In one embodiment as shown in FIG. 6A, a bar code 18 designed to be read by reflectance or fluorescence is fixed to the body of the accessory device. If it is placed on the side of the accessory device, a separate reader may be needed to scan the code. The lot number, intended use, and other pertinent information is contained in the code and interpreted by the optical scanner. In another embodiment, shown in FIG. 6B, the code 19 is fixed to a transparent part 20 of the accessory device. This permits the optical system itself to read the contents of the code 19 prior to performing its measurement of the sample (e.g., tissue). Other accessory device marker and reader combinations will be apparent to those of skill in the art, and are encompassed within the scope of the invention.

As discussed above, any or all of the foregoing options can be combined to create accessory devices suitable for particular diagnostic purposes. For example, an accessory device including optical elements can also include electrical and/or mechanical elements to disable the devise so that it can only be used a single time. Devices with optical elements and/or single-use devices can include the structural features that make an accessory device minimally invasive and/or tissue-conforming. Any and all of these combinations are encompassed within the scope of the invention.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A system for detecting features of a tissue sample, comprising:
    an optical probe; and
    an accessory device for attachment to the optical probe, wherein at least one of the probe and the accessory device includes an element for providing encoded information relating to at least one of the probe and the accessory device, wherein the element comprises a bar code for storing the encoded information.

2. The system of claim 1, wherein the element further comprises an electrical element and the encoded information is stored therein.

3. The system of claim 1, further comprising an element reader for accessing the encoded information in the element.

4. The system of claim 1, wherein the encoded information includes identification information.

5. The system of claim 1, wherein the encoded information enables particular operating modes of the device.

6. The system of claim 2, wherein the electrical element is remotely programmable.

7. The system of claim 2, wherein the electrical element includes an RFID chip.

8. The system of claim 3, wherein the element reader further comprises a processor including a memory, and wherein the processor compares identification information encoded in the element to identification information located within the memory.

9. The system of claim 8, wherein the processor transmits instructions based on whether a match is found between the identification information encoded in the element and the identification information encoded in the memory.

10. The system of claim 9, wherein if no match is found, the identification information encoded in the element is added to the memory.

11. The system of claim 9, wherein the instructions include an instruction that permits the optical probe to function if no match is found.

12. The system of claim 9, wherein the instructions include an instruction that prevents the optical probe from functioning if no match is found.

13. The system of claim 8, wherein the processor controls transmission of light by the probe.

14. The system of claim 3, wherein the element reader is attached to the probe.

15. The system of claim 3, wherein the element reader is separate from the accessory device.

16. The system of claim 3, wherein the element reader is removably attached to the probe.

17. The system of claim 1, wherein the accessory device includes a flexible portion for conforming to a body space.

18. The system of claim 1 wherein the accessory device includes an integral lens.

19. The system of claim 1 wherein the accessory device includes a body and an attachment element for attaching the accessory device to the probe, the attachment element detaching from the body of the accessory device when the accessory device is removed from the probe, thereby preventing re-use of the accessory device.

20. A system for detecting features of a tissue sample, comprising:
    an optical probe; and
    an accessory device for attachment to the optical probe, wherein at least one of the probe and the accessory device includes an element for providing encoded information relating to at least one of the probe and the accessory device, wherein the element comprises an RFID chip for storing the encoded information.

21. The system of claim 20, wherein the element is an electrical element.

22. The system of claim 20, wherein the element is remotely programmable.

23. The system of claim 20, wherein the encoded information includes identification information.

24. The system of claim 20, further comprising an element reader for accessing the encoded information in the element.

25. The system of claim 20, wherein the encoded information enables particular operating modes of the device.

26. The system of claim 20, wherein the accessory device includes a flexible portion for conforming to a body space.

27. The system of claim 20 wherein the accessory device includes an integral lens.

28. The system of claim 20, wherein the element further comprises a bar code.

29. The system of claim 20 wherein the accessory device includes a body and an attachment element for attaching the accessory device to the probe, the attachment element detaching from the body of the accessory device when the accessory device is removed from the probe, thereby preventing re-use of the accessory device.

30. The system of claim 24, wherein the element reader is attached to the probe.

31. The system of claim 24, wherein the element reader is separate from the accessory device.

32. The system of claim 24, wherein the element reader is removably attached to the probe.

33. The system of claim 24, wherein the element reader further comprises a processor including a memory, and wherein the processor compares identification information encoded in the element to identification information encoded in the memory.

34. The system of claim 33, wherein the processor transmits instructions based on whether a match is found between the identification information encoded in the element and the identification information encoded in the memory.

35. The system of claim 34, wherein if no match is found, the identification information encoded in the element is added to the memory.

36. The system of claim 33, wherein the processor controls transmission of light by the probe.

37. The system of claim 34, wherein the instructions include an instruction that permits the optical probe to function if no match is found.

38. The system of claim 34, wherein the instructions include an instruction that prevents the optical probe from functioning if no match is found.

* * * * *